United States Patent [19]

Bersin

[11] Patent Number: 5,383,856
[45] Date of Patent: Jan. 24, 1995

[54] HELICAL SPIRAL BALLOON CATHETER

[76] Inventor: Robert M. Bersin, 2005 Cortelyou Rd., Charlotte, N.C. 28203

[21] Appl. No.: 37,566

[22] Filed: Mar. 19, 1993

[51] Int. Cl.$^6$ .............................................. A61M 29/00
[52] U.S. Cl. ...................................... 604/101; 604/96; 604/103; 606/194
[58] Field of Search ..................... 604/93, 95, 96, 97, 604/98, 99, 101, 102, 103, 104; 606/191, 192, 194, 195

[56] References Cited

U.S. PATENT DOCUMENTS

| | | |
|---|---|---|
| Re. 32,983 | 7/1989 | Levy . |
| Re. 33,561 | 3/1991 | Levy . |
| 4,581,017 | 4/1986 | Sahota . |
| 4,762,130 | 8/1988 | Fogarty et al. ............... 606/194 |
| 4,787,388 | 11/1988 | Hofmann . |
| 4,934,786 | 6/1990 | Krauter ............... 604/101 |
| 4,983,167 | 1/1991 | Sahota . |
| 5,019,042 | 5/1991 | Sahota . |
| 5,090,958 | 2/1992 | Sahota . |
| 5,147,377 | 9/1992 | Sahota . |
| 5,160,321 | 11/1992 | Sahota . |
| 5,226,888 | 7/1993 | Arney . |

Primary Examiner—C. Fred Rosenbaum
Assistant Examiner—Perry E. Van Over
Attorney, Agent, or Firm—John C. Kerins

[57] ABSTRACT

A balloon catheter device designed to be especially well suited to repair or tack dissections in a blood vessel, and a method for repairing dissections, are provided, wherein the balloon catheter has a central support tube or lumen, and has, near a distal end of the catheter, a plurality of inflatable balloon elements extending along the catheter in helical patterns, with the balloon elements are spaced equidistantly around the central support tube. The catheter thus provides the ability to apply pressure, by way of the inflated balloon elements, to tack a dissection flap against the wall of the blood vessel under repair, while at the same time preserving blood flow in the blood vessel past the catheter as well as in side branch blood vessels extending from the blood vessel under repair. The helical or spiral configuration of the balloon elements provides the device with contact or bearing surfaces which closely approximates the path of spiral dissections which are known to occur in blood vessels.

6 Claims, 3 Drawing Sheets

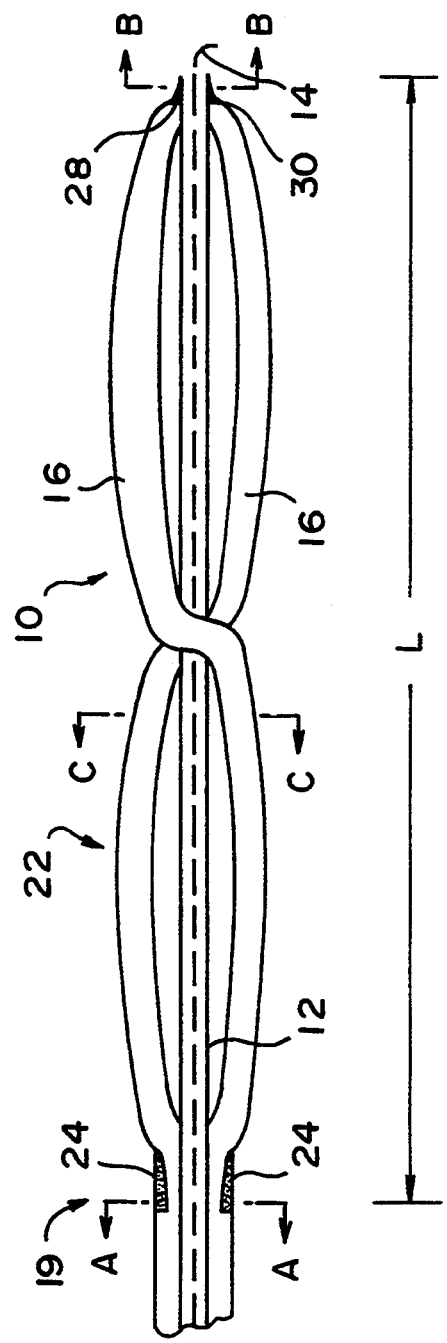
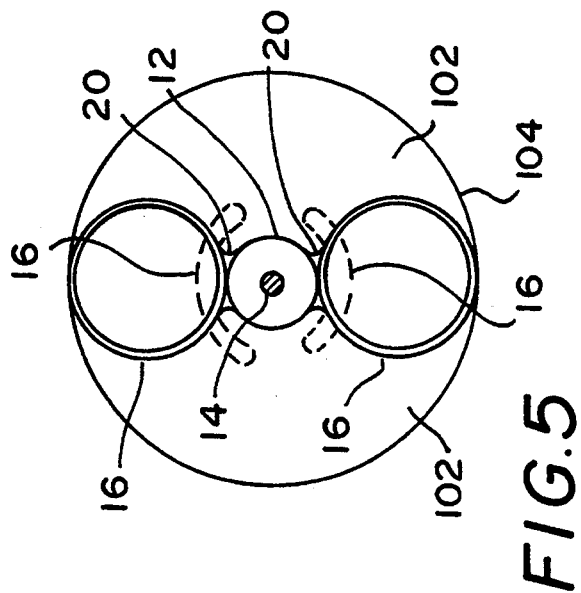
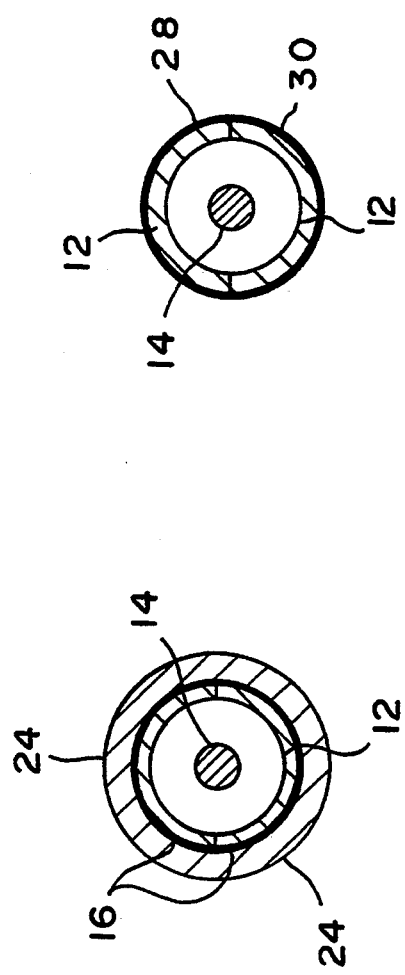
FIG. 2
FIG. 5
FIG. 4
FIG. 3

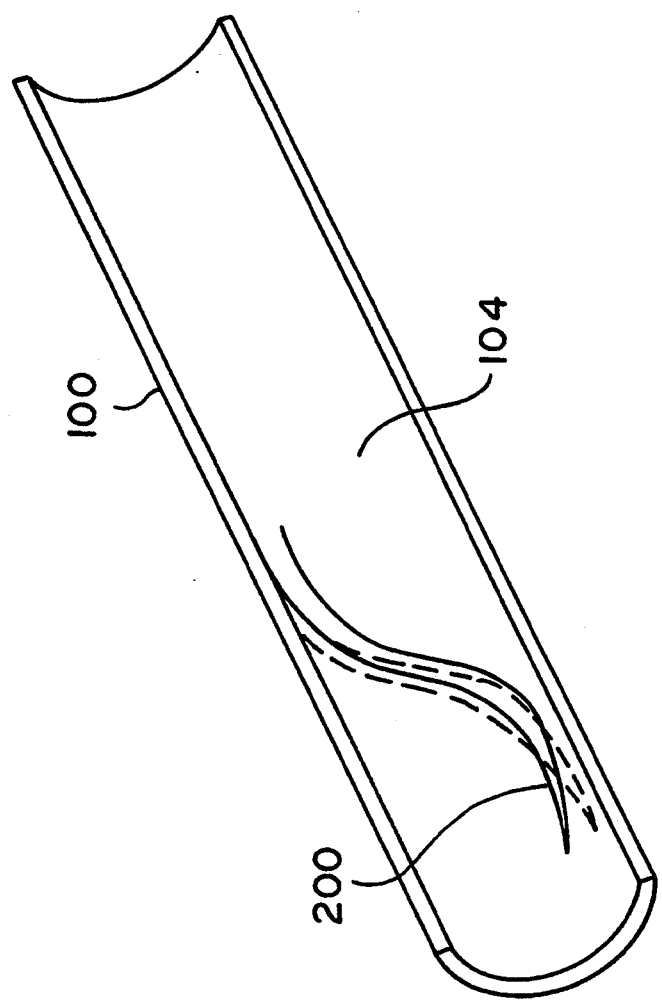

HELICAL SPIRAL BALLOON CATHETER

BACKGROUND OF THE INVENTION

1. Field of the Invention

The present invention relates to balloon catheters, and more particularly to catheters for use in repairing dissections or tears in the walls of blood vessels.

Several designs of dilatation balloon catheters have been proposed in the prior art, examples of which can be seen in U.S. Pat. Nos. 5,160,321; 5,090,958; 4,787,388; and 4,581,017. Each of those balloon dilatation catheters was designed for the purpose of administering treatments to widen constricted blood flow passages. The term stenosis is used in this regard to refer to a region of a blood vessel which has been narrowed or constricted to such a degree that blood flow is restricted. In severe instances, treatment of the stenosis is required. Treatment of coronary blood vessels by use of the aforenoted prior art dilatation balloon catheters is referred to in the art as percutaneous transluminal coronary angioplasty (PTCA), which procedure is described in various forms in the patents identified above. The term "dilatation catheter", as used herein, will refer to the type of catheter which is principally designed for use in widening constricted blood flow passages, as is done in the PTCA procedure.

One problem associated with PTCA which has been recognized in, for example, U.S. Pat. No. 4,581,017, issued to Sahota, and U.S. Pat. No. 4,787,388, issued to Hofmann, is that, in performing the PTCA procedure, blood flow cannot be completely occluded for extended periods of time, measured in terms of well under one minute, due to the increased probability that serious damage to the patient's heart or other downstream vessels or organs will occur. The Sahota patent presents two approaches to solving this problem, a first of which is to provide a balloon catheter which, even though the inflated balloon completely occludes the blood vessel, i.e., the balloon inflates into contact with the blood vessel around the entire circumference of the blood vessel, blood is permitted to flow from a proximal side of the balloon to the distal (downstream) side of the balloon through a central lumen. The second solution proposed by Sahota, which appears to be conceptually the same as the Hofmann solution, is to design the balloon such that, when the balloon is expended or inflated, it will not completely occlude blood flow, but which will, at the same time, provide sufficient area of balloon contact around the circumference of the blood vessel such that the tissue or other matter creating the constriction in the blood vessel can be compressed against the vessel wall in an effective manner. These designs purport to permit a longer dilatation period to be used when performing the PTCA procedure.

A further balloon catheter design of which the present inventor is aware is disclosed in U.S. Pat. No. 4,762,130, issued to Fogarty et al. This catheter was not designed as a dilatation catheter for use in performing the PTCA procedure, but instead was developed for use in removing blood clots from blood vessels, and also for use as a diagnostic tool carrying diagnostic equipment in a lumen or lumens associated with the catheter. The corkscrew shape of the balloon on this catheter was adopted specifically to avoid the application of diametrically opposed forces on the wall of the blood vessel, so as to minimize the possibility of abrasions and/or perforations occurring in the vessel wall. As such, this balloon catheter would be particularly unsuitable for use in performing the PTCA procedure or for other procedures requiring some amount of diametrically opposed force or other opposing forces to be applied.

It has previously been noted that dissection of the blood vessel is a potential problem in performing the PTCA procedure, and one or more of the aforenoted patents directed to dilatation catheters discuss procedural steps which attempt to minimize the possibility that dissection will occur. None of the above-noted dilatation catheter patents discusses providing a balloon-type catheter having a balloon configuration which is especially well-suited for use in repairing or tacking such dissections.

It is therefore a principal object of the present invention to provide a balloon-type catheter having features making it especially well-suited for repair operations in which blood vessel dissections are tacked back into place along the blood vessel wall.

It is a further principal object of the present invention to provide a balloon-type catheter in which a plurality of balloons are configured in a helical or spiral pattern extending around a central support tube or lumen, whereby tacking of dissections can be achieved while preserving blood flow down the main trunk or blood vessel, and also in side branches extending from the main trunk.

SUMMARY OF THE INVENTION

The present invention provides a balloon catheter configuration whose primary purpose is not the dilatation of constricted portions of blood vessels, but is instead the repair or tacking of dissections in the blood vessel which have been created during the dilatation of the blood vessel in the PTCA procedure, or which have otherwise been created and exist in a blood vessel.

The balloon catheter of the present invention provides a configuration which further permits continued perfusion along the main blood vessel in which the repair operation is being performed, and provides improved protection of flow to side branch blood vessels extending from the main blood vessel under repair, all while the balloons of the catheter are expanded or inflated and are performing their repair function. Both of these features have been determined to be of substantial importance in a balloon catheter whose principal purpose is to repair or tack dissections, in that such repair may require the catheter to be in place with its balloons expanded or inflated for considerable periods of time.

In one or more of the above-noted patents disclosing dilatation catheter devices, the desirability of retaining blood flow down the main blood vessel being treated was recognized, even for relatively short-term occlusion of the blood vessel by the catheter. However, none of those patents discuss the importance of protecting (by preserving) blood flow into side branch vessels. This is likely due to the fact that the dilatation balloon catheters, even when inflated for what would be considered to be extended periods of time in the PTCA procedure, would be inflated and blocking off most, if not all, side branch flow for a time measured in terms of seconds, or at most in terms of a couple of minutes. In contrast, the repair or tacking of a dissection may require on the order of one to several hours or up to approximately one day or more. A continuous inflation of the balloon or balloons on the repair catheter device is important to obtaining the highest quality repair of the blood vessel in the shortest time possible, and thus being able to leave the device in place with the balloon(s) inflated for extended periods of time is an important feature. Preserving the blood flow to the side branches, which is not as critical over lengths of time on the order of several seconds to several minutes, becomes a very important consideration when longer time periods are involved, and is thus a very important consideration in the design of the balloon catheter of the present invention.

The balloon catheter of the present invention has the additional advantage, as respects the use of the catheter in repairing blood vessel dissections, that the balloon elements are arranged such that the balloon elements, when expanded or inflated, present helical or spiral bearing or contact surfaces which will conform to or closely approximate the dissection path of one of the most commonly experienced dissection modes resulting from performing the PTCA process.

BRIEF DESCRIPTION OF THE DRAWINGS

These and other features of the present invention and the attendant advantages will be readily apparent to those having ordinary skill in the art and the invention will be more easily understood from the following detailed description of the preferred embodiments of the present invention taken in conjunction with the accompanying drawings, wherein like reference characters represent like parts throughout the several views.

FIG. 2 is an schematic elevational view of the helical balloon catheter of the present invention.

FIG. 3 is a cross-sectional view of the helical balloon catheter of the present invention taken along section line A—A of FIG. 2.

FIG. 4 is a cross-sectional view of the helical balloon catheter of the present invention taken along section line B—B of FIG. 2.

FIG. 5 is a cross-sectional view of the helical balloon catheter of the present invention taken along section line C—C of FIG. 2.

FIG. 6 is a cross-sectional view of the helical balloon catheter of the present invention taken along section Line D—D of FIG. 1.

FIG. 7 is a perspective cutaway view of a blood vessel schematically illustrating a spiral or helical dissection formed therein.

DETAILED DESCRIPTION OF THE PREFERRED EMBODIMENT

Figure 1:
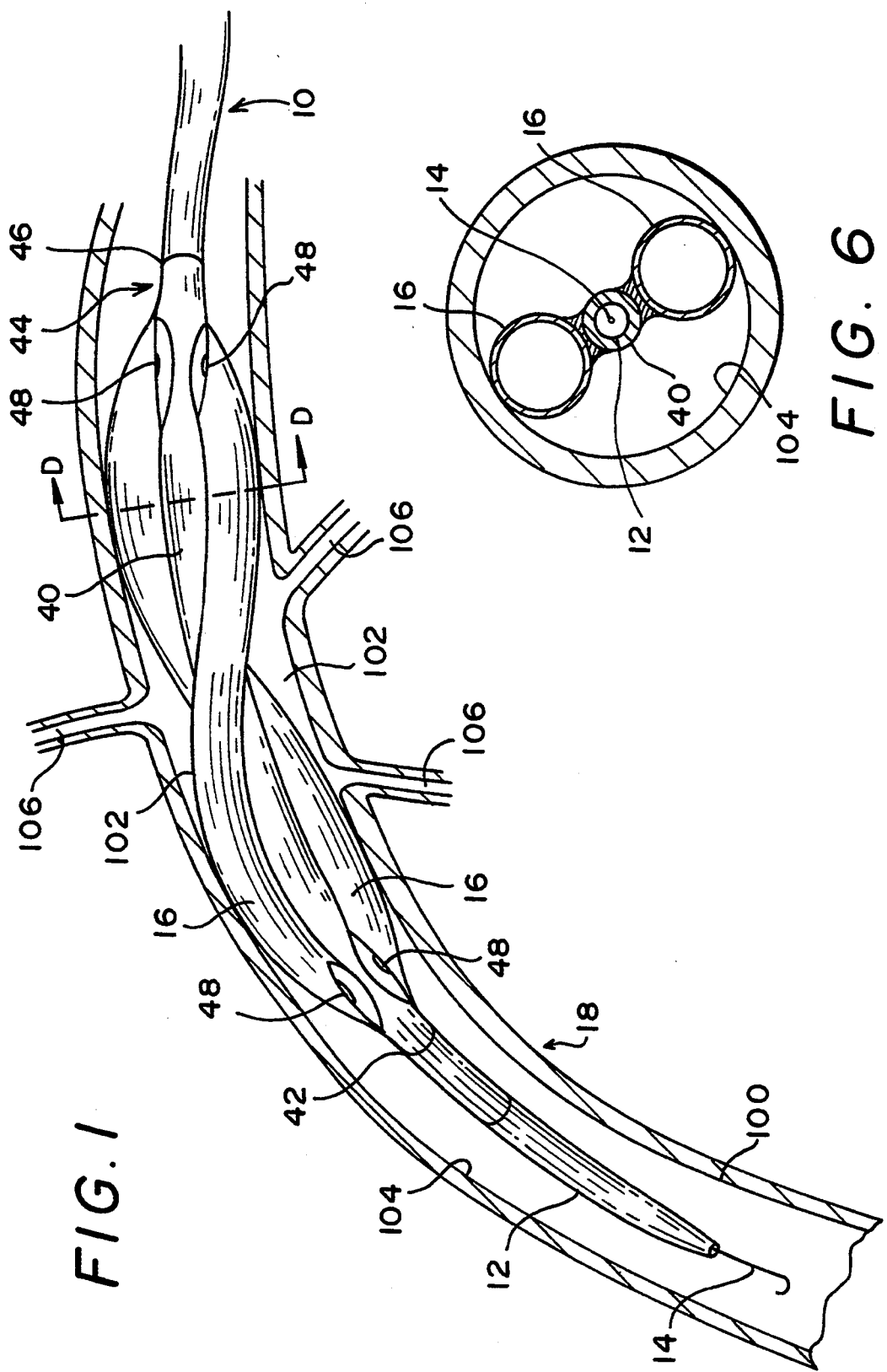
FIG. 1 is an elevational view of the helical balloon catheter of the present invention as disposed and inflated in a blood vessel which is depicted in cross-section.

Referring initially to FIGS. 1 and 2, the multiple helical balloon catheter is designated by numeral 10. Catheter 10 has a central support tube defining a central lumen 12 adapted to carry therein a guide or advance wire 14 which, as is generally known in the art, is used to facilitate insertion of the catheter to the desired position within the blood vessel. In the present invention, because the device will be used primarily for repair of dissections in blood vessels, the desired position for the catheter in the blood vessel will ordinarily be at the site where the dissection has occurred and/or has been detected.

Disposed at the outer surface of the central lumen 12, and extending therealong in a longitudinal direction, are a plurality of balloon elements 16. The depicted preferred embodiment employs two such balloon elements. The balloon elements 16 are preferably disposed near a distal end 18 of the catheter. The balloon elements 16 are also preferably arranged in a "double helix", wherein two diametrically opposed spiraling or helical balloon elements wind around the central support tube and lumen 12. The balloon elements 16 are preferably bonded to the outer surface of the central lumen with a suitable cement or adhesive 20 (see FIG. 5), along the entire longitudinal extent of the elements, in order to retain the double helical orientation and positioning with respect to the central lumen throughout the insertion and repair procedure. This bonding can be continuous along the longitudinal extent or the adhesive 20 can be applied at substantially regular intervals along the longitudinal extent.

FIGS. 2-5 illustrate preferred constructional features of the double (two balloon segments) helical balloon catheter 10 in one of the preferred embodiments of the present invention. As can be seen in FIG. 2, the central lumen 12 is preferably fluidically isolated from the balloon elements 16 and the means for inflating or expanding the balloon elements. At a proximal end 19 of the balloon subassembly 22, a fluid supply sleeve 24, also referred to as an inflation port, surrounds the central lumen and is coupled to the balloon elements 16 in a fluid-tight connection. The fluid supply sleeve 24 is shown as being coextensive and concentric with the central support tube or lumen 12 and the sleeve extends to the outside of the body. It should be recognized that the fluid supply sleeve (inflation port) and central support tube or lumen 12 can be arranged in many other preferred constructions, one further example of which is an approximately crescent-shaped inflation port extending along the central support tube, wherein the inner portion of the inflation port is integral with, or conforms to and is contact with, the outer surface of the central support tube. The inflation fluid, generally a solution of saline and a contrast agent, is supplied to the balloon elements through this sleeve 24.

The proximal ends of balloon elements 16 are fluidly coupled to and extend toward a distal end of the catheter from the fluid supply sleeve 24. The sleeve acts generally in the nature of an inextensible (under the range of fluid pressures experienced in this service) collar. As can be seen in FIG. 3, the proximal end of each of the balloon elements 16 occupies substantially one-half of the area between central lumen 16 and sleeve 24. When the inflating fluid is transmitted to sleeve 24, the flow of fluid is thus essentially evenly divided into each of the two balloon elements 16. It may be preferred, from a manufacturing standpoint, to produce the sleeve 24 and the balloon elements 16 as an integral unit in an extrusion process.

The balloon elements 16 extend from the fluid supply sleeve 24 in diametrically opposed helical paths toward the distal end of catheter 10. It is to be noted that, for ease of illustration, the balloon elements 16 in FIG. 2 are shown as not being bonded to the central support tube 12, however, as previously noted, these elements 16 are required to be bonded to the central member, at least at intermittent points along their extent.

At a distal end of the balloon elements 16, the ends 28, 30 of the elements are sealed down against the outer surface of the support tube or central lumen 12 (FIGS. 2,4) to ensure that the inflating fluid transmitted into the balloon elements is retained therein to expand or inflate the balloons.

Other means of attaching the balloon elements to the catheter and for supplying fluid into the elements will be readily envisioned by those skilled in the balloon catheter art. FIG. 1, for example, depicts a variation on the construction illustrated in FIGS. 2-5. In FIG. 1, the central support tube or lumen 12 is provided with a fluid supply tube 40 which does not terminate at the proximal end of the balloon elements, as does sleeve 24 in FIG. 2, but further extends concentrically around and along the central lumen for a distance somewhat greater than the longitudinal extent of the balloon elements 16. Supply tube 40 is sealed against the central lumen 12 at its distal end 42, and is coupled at its proximal end 44 to a fluid supply conduit 46 which extends concentrically with along central lumen 12 to a point outside the patient's body, where it is coupled to means for supplying fluid to inflate the balloon elements 16. This fluid supply conduit 46 operates much in the same manner as does sleeve 24 in the FIG. 2 embodiment.

Supply tube 40 has bonded thereto the two balloon elements 16, with the open proximal and distal ends of the balloon elements being connected in a fluid-tight manner to tube 40. Tube 40 is provided with fluid openings 48 at its proximal and distal ends which place the tube 40 in fluid communication with the proximal and distal ends of balloon elements 16. Fluid delivered through conduit 46 enters tube 40 and passes through openings 48 to inflate the balloon elements to the desired pressure. It is to be noted that, in this alternative preferred embodiment, the supply tube 40 is substantially inextensible as compared with the balloon elements 16, such that the inflating fluid supplied inflates the balloon-elements without substantially inflating or expanding the diameter of the tube 40. As with the FIG. 2 embodiment, it may be preferred to form the entire FIG. 1 structure as an integral unit in an extrusion process.

FIG. 5 illustrates, in somewhat schematic form, the cross-section of double helical balloon catheter shown in FIG. 1. The balloon elements 16 are shown in solid lines in their inflated or expanded condition, and are shown in broken lines in their unexpanded condition. The inner wall of the blood vessel is schematically represented by circle 104 in FIG. 5. It can be seen that, at any given point along the longitudinal extent of the balloon elements, a path for the flow of blood through the blood vessel undergoing repair is provided around the outer surfaces of the central support tube or lumen 12, and the expanded or inflated balloon elements 16. The cross-section shown in FIG. 6 is essentially the same as that of FIG. 5, with the exception that the concentric arrangement of the central support tube or lumen 12 and fluid supply tube 40 can be seen in FIG. 6, with the balloon elements being bonded to the outer tube 40.

The use and operation of the double helical balloon catheter device as a blood vessel repair tool will now be described with reference to all figures, but in particular FIGS. 1 and 7. As shown in FIG. 1, the balloon elements 16 are in position and are expanded or inflated, which brings the outer surfaces thereof into contact with the inner wall 104 of the blood vessel 100. It will be readily understood to those of ordinary skill in this field of art that when the catheter is being inserted through the blood vessel to its desired position, the balloon elements 16 will not be inflated (see broken lines, FIG. 5) and the catheter can thus be inserted through the blood vessel without any substantial and potentially damaging scraping or rubbing of the balloons against the walls of the blood vessel. In this respect, techniques for inserting dilatation balloon catheters as have been previously disclosed in the art will generally be applicable to the insertion of the balloon catheter of the present invention, and no detailed discussion of such techniques thus will be included herein.

FIG. 1 illustrates that the balloon catheter 10 of the present invention provides a relatively open blood flow path down the main trunk or blood vessel 100, wherein the blood flowing past the balloon catheter 10 moves through the two approximately helically extending cavities 102 created by the outer surfaces of the balloon elements 16 and central lumen 12, and bordered by the inner wall 104 of the blood vessel 100 (see also FIG. 5).

The method for repairing a dissection at an inner wall of a blood vessel with the device of the present invention involves inserting the catheter 10 into the cardiovascular system of a patient to be treated, with the balloon elements 16 being in their unexpanded or uninflated condition. The distal end of the catheter with guide wire 14 protruding therefrom is first inserted, and the catheter is advanced within the cardiovascular system until the balloon elements are situated in the region within the blood vessel to be repaired where the dissection has been detected. The catheter is then oriented, by rotating the catheter as necessary, such that one of the two balloon elements is positioned immediately adjacent to, but not necessarily touching, the dissection to be repaired. At this point, the balloon elements 16 are expanded or inflated to bring the outer or bearing surface 17 of the balloon element 16 adjacent the dissection into intimate contact with the dissection, which also will bring the other balloon into contact with the wall of the blood vessel at a point substantially diametrically opposite the dissection. The applied pressure is thus focused on the flap 200 (FIG. 7) formed by the dissection, urging the flap 200 back into the vessel wall from which it has become detached.

With the balloon elements thus inflated, blood is permitted to continue flowing past the balloon elements 16 along the main trunk, and into unobstructed side branches in the area at which the balloon elements are disposed. The balloons are left in their inflated or expanded condition for a length of time, most likely on the order of tens of minutes to several hours, which is estimated in advance to be sufficiently long to obtain a substantially permanent tacking of the flap against the inner wall 104 of the blood vessel 100. After that time period has elapsed, the balloon elements are brought back to their uninflated or unexpanded state, and the catheter may then be withdrawn.

It will be readily apparent that various diagnoses may be made with respect to determining whether the tacking of the dissection flap 200 has been successfully accomplished prior to the removal of the catheter, and it is expected that such diagnostic procedures will be so employed.

FIG. 7 illustrates flap 200 resulting from the dissection in the blood vessel wall. The dissection commonly appears in an approximately helical pattern, as is shown. The balloon catheter of the present invention thus is very well suited to repair such dissections, as the helically extending balloon elements 16 can be positioned such that pressure is brought to bear against the flap 200 along most, if not all, of its entire length.

By providing an open helical path for blood to flow along the blood vessel under repair, the device permits the use of balloons which extend along a greater length L (FIG. 2) than the balloons employed on prior dilatation catheters. The preferred length L of the balloons on the present device is on the order of 40 centimeters, as compared with a 10–20 centimeter balloon length in existing commercial dilatation catheters. As can be seen in referring back to FIG. 1, the design of the helical balloon catheter of the present invention preserves blood flow to side branches 106 extending off of the blood vessel under repair, even though the balloons are of a greater length than those previously employed in dilatation catheters.

Other variations on the illustrated preferred embodiments are possible. The balloon elements 16 as shown have a round cross-sectional shape, however, other shapes, such as triangles, may be employed as well. A preferred material of construction for the catheter of the present invention is high density polyethylene, although other materials may be suitable for use. The construction of the device can be modified, if desired, to provide the capability to independently inflate each balloon element. Lastly, while the catheter 10 is shown in the preferred embodiments as having two diametrically opposed balloon elements 16 extending in a helical pattern, it may be possible to employ three or more helically-extending balloon elements which are spaced equidistantly around the central support tube 12.

The foregoing description is provided for illustrative purposes only, and variations and modifications to the depicted and described preferred embodiments may become readily apparent to those of ordinary skill in the art without departing from the spirit and scope of the present invention. Accordingly, the scope of the invention is to be determined by reference to the appended claims.

What is claimed:

1. A method for repairing a dissection in an inner wall of a blood vessel in a patient comprising the steps of:
   (a) providing a catheter comprising an elongated support tube having distal and proximal ends, said support tube defining a central lumen, a radially expandable balloon means carried by and integrally connected to said support tube adjacent the distal end thereof, and means for expanding and contracting said balloon means, said balloon means comprising at least two spiral-shaped balloon elements extending helically around said support tube along a predetermined length of said support tube;
   (b) inserting said distal end of said catheter into a cardiovascular system of said patient with said balloon means in an unexpanded condition;
   (c) advancing said catheter within said cardiovascular system until said balloon means is situated in the region having the dissection needing repair;
   (d) orienting said catheter such that a first one of said at least two balloon elements is positioned to overlie said dissection;
   (e) expanding said balloon means to bring said first one of said balloon elements into intimate contact with said blood vessel dissection, and to bring each other of said at least two balloon elements into intimate contact with said blood vessel, while permitting the patient's blood to flow past the balloon means through open paths left between said balloon elements, and permitting the patient's blood to flow to unobstructed side branches in the region in which the balloon means is disposed;
   (f) retaining said balloon elements in said expanded condition for a length of time sufficient to tack said dissection substantially permanently into place along an inner wall of said blood vessel;
   (g) contracting the balloon means; and
   (h) withdrawing said catheter from the body of said patient.

2. The method as set forth in claim 1, wherein said balloon means comprises only two balloon elements, and said two balloon elements extend in diametrically opposed helical paths along said support tube.

3. A dissection repair balloon catheter comprising:
   a central support tube;
   a plurality of balloon elements disposed at a distal end of said central support tube;
   each of said plurality of balloon elements having a longitudinal extent, each of said plurality of balloon elements winding around said central support tube in a helical pattern, wherein said plurality of balloon elements are spaced equidistantly around a circumference of said central support tube; and
   means fluidly coupled to said balloon elements for expanding said balloon elements into contact with an inner wall of a blood vessel of a patient when said catheter and said balloon elements are in a desired position within said blood vessel; and
   means for returning said balloons to an unexpanded condition.

4. A dissection repair balloon catheter as recited in claim 3, wherein said plurality of balloon elements consists of only two balloon elements disposed in diametrically opposed helical patterns.

5. A dissection repair balloon catheter as recited in claim 3, wherein each of said plurality of balloon elements is bonded to said central support tube along substantially an entire length of said balloon.

6. A dissection repair balloon catheter as recited in claim 3, further comprising a guide wire removably housed within said central support tube.

* * * * *